(12) United States Patent
Kelson et al.

(10) Patent No.: US 12,138,474 B2
(45) Date of Patent: Nov. 12, 2024

(54) RADIOTHERAPY SEEDS AND APPLICATORS

(71) Applicant: Alpha Tau Medical Ltd., Tel Aviv (IL)

(72) Inventors: Itzhak Kelson, Tel Aviv (IL); Yona Keisari, Ramat Gan (IL); Michael Schmidt, Kfar Saba (IL); Ofer Magen, Hod Hasharon (IL); Amitai Sosnovitch, Nodkim (IL); Guy Keret, Beit Yehoshua (IL); Amnon Gat, Matan (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 972 days.

(21) Appl. No.: 16/968,646

(22) PCT Filed: Mar. 7, 2019

(86) PCT No.: PCT/IB2019/051834
§ 371 (c)(1),
(2) Date: Aug. 10, 2020

(87) PCT Pub. No.: WO2019/171308
PCT Pub. Date: Sep. 12, 2019

(65) Prior Publication Data
US 2020/0406059 A1    Dec. 31, 2020

Related U.S. Application Data

(60) Provisional application No. 62/640,077, filed on Mar. 8, 2018.

(51) Int. Cl.
*A61N 5/00*    (2006.01)
*A61L 2/04*    (2006.01)
*A61N 5/10*    (2006.01)

(52) U.S. Cl.
CPC ............. *A61N 5/1007* (2013.01); *A61L 2/04* (2013.01); *A61N 5/1027* (2013.01);
(Continued)

(58) Field of Classification Search
CPC ...... A61N 2005/1009; A61N 2005/101; A61N 2005/1011; A61N 2005/1024;
(Continued)

(56) References Cited

U.S. PATENT DOCUMENTS 2,075,508 A    3/1937    Davidson
5,899,882 A    5/1999    Waksman et al.
(Continued)

FOREIGN PATENT DOCUMENTS

AU    2003262506 B2    5/2007
CN    104162226 A    11/2014
(Continued)

OTHER PUBLICATIONS

EP Application # 19763461.1 Search Report dated Nov. 2, 2021.
(Continued)

*Primary Examiner* — Dani Fox
(74) *Attorney, Agent, or Firm* — MEITAR PATENTS LTD.

(57) ABSTRACT

A casing holding one or more brachytherapy seeds for implanting in a patient, which in turn carry atoms of a radioactive element for radiotherapy treatment is filled with a viscous liquid in a manner preventing radiation from the one or more brachytherapy seeds from exiting the casing. The casing may include a metallic or non-metallic elongated tube configured for insertion into tissue or a vial for delivering a seed to a physician for insertion into a needle.

33 Claims, 6 Drawing Sheets

(52) U.S. Cl.
CPC .............................. *A61N 2005/101* (2013.01); *A61N 2005/1024* (2013.01); *A61N 2005/1098* (2013.01)

(58) Field of Classification Search
CPC .... A61N 2005/1094; A61N 2005/1098; A61N 5/1007; A61N 5/1027
See application file for complete search history.

(56) References Cited

U.S. PATENT DOCUMENTS

| | | | |
|---|---|---|---|
| 6,752,753 | B1 | 6/2004 | Hoskins et al. |
| 7,497,818 | B2 | 3/2009 | Terwilliger et al. |
| 8,834,837 | B2 | 9/2014 | Kelson et al. |
| 9,272,160 | B2 | 3/2016 | Kader et al. |
| 10,888,710 | B1 | 1/2021 | Brachman et al. |
| 2003/0088144 | A1 | 5/2003 | Terwilliger et al. |
| 2003/0109769 | A1 | 6/2003 | Lowery et al. |
| 2003/0139700 | A1* | 7/2003 | Elliott ................ A61N 5/1007 604/62 |
| 2003/0191355 | A1 | 10/2003 | Ferguson |
| 2005/0184424 | A1 | 8/2005 | Ferguson |
| 2005/0267319 | A1 | 12/2005 | White et al. |
| 2006/0235365 | A1 | 10/2006 | Terwilliger et al. |
| 2008/0004483 | A1 | 1/2008 | Tarone et al. |
| 2008/0269540 | A1 | 10/2008 | Lamoureux |
| 2009/0136422 | A1 | 5/2009 | Kelson et al. |
| 2009/0187061 | A1 | 7/2009 | Barber et al. |
| 2009/0216064 | A1 | 8/2009 | Lebovic et al. |
| 2010/0249487 | A1 | 9/2010 | Hermann et al. |
| 2011/0206603 | A1* | 8/2011 | Peng ................ A61K 51/1217 424/9.4 |
| 2014/0048729 | A1 | 2/2014 | Johansson et al. |
| 2014/0296612 | A1 | 10/2014 | Schwartz |
| 2015/0360019 | A1 | 12/2015 | Clancy et al. |
| 2015/0375011 | A1 | 12/2015 | Spittle et al. |
| 2017/0319871 | A1 | 11/2017 | Pitman |
| 2018/0082760 | A1 | 3/2018 | Abernethy et al. |
| 2019/0099618 | A1 | 4/2019 | Stauffer et al. |

FOREIGN PATENT DOCUMENTS

| | | | |
|---|---|---|---|
| EP | 1082729 | B1 | 8/2004 |
| GB | 681938 | A | 10/1952 |
| JP | 2014061188 | A | 4/2014 |
| JP | 2017000341 | A | 1/2017 |
| RU | 2599684 | C1 | 10/2016 |
| WO | 9737715 | A1 | 10/1997 |
| WO | 0004953 | A2 | 2/2000 |
| WO | 2004082762 | A1 | 9/2004 |
| WO | 2004096293 | A2 | 11/2004 |
| WO | 2005002670 | A1 | 1/2005 |
| WO | 2005087274 | A1 | 9/2005 |
| WO | 2009156893 | A1 | 12/2009 |
| WO | 2012002815 | A1 | 1/2012 |
| WO | 2014189604 | A2 | 11/2014 |
| WO | 2017157879 | A1 | 9/2017 |
| WO | 2017157880 | A1 | 9/2017 |
| WO | 2017173352 | A1 | 10/2017 |
| WO | 2019171308 | A1 | 9/2019 |

OTHER PUBLICATIONS

CN Application # 201980016928.X Office Action dated Dec. 3, 2021.
CN Application # 201980016928X Office Action dated Jul. 13, 2022.
AU Application # 2021236578 Office Action dated Jul. 20, 2022.
AU Application # 2021236577 Office Action dated Aug. 2, 2022.
AP Application # AP/P/2020/012637 Office Action dated Sep. 8, 2022.
CN Application # 201980016928X Office Action dated Jan. 5, 2023.
AU Application # 2019229849 Office Action dated May 7, 2021.
IN Application # 202047034605 Office Action dated Jun. 5, 2021.
JP Application # 2020544280 Office Action dated Aug. 16, 2023.
RU Application # 2023105580 Office Action dated Aug. 30, 2023.
RU Application # 2023105576 Office Action dated Aug. 1, 2023.
RU Application # 2023105578 Office Action dated Jul. 31, 2023.
SG Application # 11202007645T Office Action dated Feb. 10, 2022.
Hofz, "A Survey of Actuator Shaft Sealing Techniques for Extended Space Missions", Technical Memorandum 33-587, National Aeronautics and Space Administration, California Institute of Technology, Pasadena, USA, pp. 1-38, Dec. 15, 1972.
International Application PCT/IB2019/051834 Search Report dated Jun. 17, 2019.
RU Application # 2020127039 Office Action dated Sep. 30, 2022.
IN Application # 202047034605 Hearing Notice dated Oct. 27, 2022.
JP Application # 2020544280 Office Action dated Nov. 30, 2022.
KR Application # 1020207026476 Office Action dated Nov. 20, 2023.
AU Application # 2023201498 Office Action dated Dec. 21, 2023.
SG Application # 11202007645T Office Action dated Mar. 8, 2024.
AP Application # AP/P/2020/012637 Office Action dated Mar. 14, 2024.
CA Application # 3091560 Office Action dated Jun. 12, 2024.

* cited by examiner

RADIOTHERAPY SEEDS AND APPLICATORS

FIELD OF THE INVENTION

The present invention relates generally to radiotherapy and particularly to methods of applying alpha particle seeds to patients.

BACKGROUND OF THE INVENTION

Brachytherapy is a powerful means for radiotherapy of certain types of tumors, including malignant tumors. Proper delivery of seeds with embedded particle emitters is important to the success of the therapy. The delivery should accurately position the seeds inside the tumor, without premature exposure of tissue of the patient and others to radioactive and otherwise unhealthy substances.

US patent publication 2015/0375011, the disclosure of which is incorporated herein by reference in its entirety, describes a brachytherapy seed with bimetallic strips that will "curl up" when exposed to body temperatures for fixing a seed in its proper location.

In many cases, brachytherapy devices are implanted permanently in the tumor and are not removed.

US patent publication 2003/0088144 to Terwilliger et al., titled: "Improved Delivery System and Method for Interstitial Radiotherapy Using Hollow Seeds", the disclosure of which is incorporated herein by reference in its entirety, suggests using a bio-absorbable seed strand on which a plurality of tubular shaped, hollow radioactive seeds are mounted.

In other cases, brachytherapy devices are implanted for short durations, generally up to several hours, in what is referred to as temporary brachytherapy.

U.S. Pat. No. 9,272,160 to Kader et al., the disclosure of which is incorporated herein by reference in its entirety, describes a brachytherapy strand with a tether, which may be used for removal of the strand.

US patent publication 2010/0249487, the disclosure of which is incorporated herein by reference in its entirety, describes a flexible brachytherapy device to be implanted in a body, with a tail portion extending outside the body. The tail portion may be used for removal of the brachytherapy device at therapy completion.

There have been suggestions to use a hollow needle and a stylet to deliver seeds to an implant location in a tumor.

US patent publication 2003/0191355 to Ferguson, the disclosure of which is incorporated herein by reference in its entirety, describes delivery of a seed array in a needle using a stylet.

US patent publication 2008/0269540 to Lamoureux, the disclosure of which is incorporated herein by reference in its entirety, describes urging seeds and optional spacers from a seed cartridge assembly, through a hollow needle, to a distal end of the hollow needle; and retracting the hollow needle, while a stylet is held in place, to thereby deposit the seeds and optional spacers at a desired location. Reference is made to a long stylet as well as a shorter stylet.

U.S. Pat. No. 6,752,753 to Hoskins et al., the disclosure of which is incorporated herein by reference in its entirety, describes a needle and stylet for delivering seeds to a tumor.

An important issue in utilization of brachytherapy devices is protection of healthy tissue from undesired radiation.

US patent publication 2014/0048729, the disclosure of which is incorporated herein by reference in its entirety, describes a light weight protection device to be worn on sensitive body organs.

US patent publication 2018/0082760, the disclosure of which is incorporated herein by reference in its entirety, describes a transparent radiation shield.

SUMMARY OF THE INVENTION

An aspect of some embodiments of the invention provides an apparatus for brachytherapy, including a casing, one or more brachytherapy seeds for implanting in a patient, carrying atoms of a radioactive element for radiotherapy treatment, within the casing, and a viscous liquid within the casing, in a manner preventing radiation from the one or more brachytherapy seeds from exiting the casing. Optionally, the casing comprises a needle. Alternatively, the casing comprises a seed applicator including a tube adapted for insertion into a patient and a stylet within the tube. Further alternatively, the casing comprises a seed capsule including a needle port on a first end and a piston carrying the one or more brachytherapy seeds on a second end, and movement of the piston urges the one or more brachytherapy seeds into a needle in the needle port.

Optionally, the viscous liquid comprises glycerine. Optionally, the casing comprises a hub at a proximal end of the elongate tube, wherein the hub has an empty chamber configured to collect excess viscous liquid from the elongate tube when the viscous liquid expands due to heat sterilization. Optionally, a distal end of the hub connecting to the elongate tube has a funnel shape configured to allow viscous liquid from the elongate tube entering the hub to return back to the elongate tube. Optionally, the needle port is configured to receive the needle in an orientation such that the one or more brachytherapy seeds enter the needle along with a portion of the viscous liquid.

There is further provided in accordance with embodiments of the invention, a method of loading a needle with brachytherapy seeds, comprising grasping a needle, having a sharp tip for entering tissue, in a manner preventing movement of the needle, bringing a brachytherapy seed to a point adjacent the tip of the needle and pushing the brachytherapy seed forward into the needle, through the sharp tip.

Optionally, pushing the brachytherapy seed forward comprises pushing a stylet, which pushes the seed forward into the needle.

There is further provided in accordance with embodiments of the invention, a brachytherapy seed loading device, comprising a central chamber storing a brachytherapy seed, a needle port, configured to lock a needle in an orientation such that a sharp tip of the needle is aligned with the brachytherapy seed in the central chamber, and a piston configured to push the brachytherapy seed into the needle locked in the needle port.

Optionally, the central chamber additionally stores a viscous liquid, which prevents Radon released by the brachytherapy seed from leaving the loading device. Optionally, the needle port includes a screw which when fastened locks the needle in the needle port. Optionally, the device includes a piston screw which when rotated pushes the piston toward the central chamber.

There is further provided in accordance with embodiments of the invention, a brachytherapy seed applicator, comprising a non-metallic elongated tube configured for insertion into tissue, a hub at a proximal end of the tube, one or more brachytherapy seeds carrying radioactive particles, within the tube, and a stylet configured to be inserted into the tube and to push the one or more brachytherapy seeds to a distal end of the elongated tube.

Optionally, the one or more brachytherapy seeds carry alpha-emitting particles. Optionally, one or more brachytherapy seeds carry Radium seeds. Optionally, the non-metallic elongated tube allows viewing of the one or more brachytherapy seeds in an ultrasound image of the applicator. Optionally, the non-metallic elongated tube prevents daughter nuclei of the radioactive particles from exiting the non-metallic elongated tube. Optionally, the one or more brachytherapy seeds are distanced from a distal tip of the non-metallic elongated tube by at least one centimeter. Optionally, the non-metallic elongated tube comprises Kapton.

There is further provided in accordance with embodiments of the invention, a stopper for controlling movement of a stylet relative to a brachytherapy needle, comprising a body structure, a first connector on the body structure, for grasping a needle hub of the brachytherapy needle, a second connector on the body structure, for grasping a stylet hub in a manner preventing the stylet from moving distally; and a third connector on the body structure, for grasping the stylet hub in a manner preventing the stylet from moving both proximally and distally.

Optionally, the first connector comprises a slot configured to grasp the needle hub. Optionally, the second connector is configured to prevent distal movement of the stylet without preventing proximal movement of the stylet. Optionally, the second and third connectors are configured to grasp the stylet hub at different axial positions relative to the needle. Optionally, the body structure is expandable in a manner changing the axial position at which the second and third connectors grasp the stylet hub.

There is further provided in accordance with embodiments of the invention, a method of inserting a brachytherapy seed into body tissue, comprising providing a needle with a brachytherapy seed therein, with a stylet inserted through a proximal end of the needle and with a stopper holding a hub of the stylet in a first connector of the stylet, which prevents both distal and proximal movement of the stylet relative to the needle, inserting a tip of the needle into a tumor, pushing the hub of the stylet out of the first connector into a second connector, which prevents distal movement of the stylet hub in a different axial position of the stylet hub relative to the needle, than the first connector; and removing the stopper, to allow retraction of the needle proximally relative to the stylet, in a manner leaving the seed within the tumor.

There is further provided in accordance with embodiments of the invention, a brachytherapy implant, comprising a hollow biocompatible wire, at least one tubular seed defining an internal channel, mounted on the hollow biocompatible wire; and radioactive particles for radiotherapy treatment placed on the at least one tubular seed.

Optionally, the hollow biocompatible wire defines an internal channel having a diameter of less than 0.5 millimeters. Optionally, the hollow biocompatible wire is not biodegradable. Optionally, the at least one tubular seed is located in the middle of the hollow biocompatible wire, at least 10 millimeters from both ends of the hollow biocompatible wire.

There is further provided in accordance with embodiments of the invention, a method of inserting a brachytherapy seed into body tissue, comprising inserting a needle into body tissue through a first point until a tip of the needle exits the tissue at a second point, pushing a distal end of a strand carrying one or more brachytherapy seeds out of the distal tip of the needle, grasping the distal end of the strand and retrieving the needle proximally from the tissue while grasping the distal end of the strand, so that the one or more brachytherapy seeds remain in the tissue. Optionally, the method includes pulling the distal end of the strand to adjust a location of the one or more brachytherapy seeds in the tissue. Optionally, grasping the distal end of the strand comprises grasping with forceps. Optionally, inserting the needle into body tissue comprises inserting the needle with the strand therein.

DETAILED DESCRIPTION OF EMBODIMENTS

An aspect of some embodiments of the invention relates to packaging of radiotherapy seeds in a package in which they are surrounded by a viscous liquid which prevents unwanted dissipation of particles from the seed. Optionally, the viscous liquid prevents release of daughter nuclei, such as Radon (Rn)-220, which escaped the seeds from the package. The viscous liquid optionally does not boil during heat sterilization. In some embodiments, the viscous liquid comprises a biocompatible glycerine, optionally USP Class VI Glycerine.

In some embodiments, the seeds are provided preloaded in an elongated delivery tube of an applicator device, and the elongated delivery tube is filled with the viscous liquid. The viscous liquid collects daughter nuclei released from the seeds. When the seeds are inserted into a tumor, the viscous liquid enters the tumor with the seeds, and radioactive daughter nuclei in the viscous liquid participate in the brachytherapy treatment.

In some embodiments, the elongate tube is a flexible tube which can be used to reach locations which are difficult to reach with a rigid needle. In other embodiments, the elongated delivery tube comprises a needle which defines an internal delivery channel. Optionally, the seeds are preloaded on a delivery wire, for example a biocompatible string suture or a metal (e.g., stainless-steel, nitinol) wire, in the tube.

The applicator device optionally includes at a proximal side of the needle or other elongate tube, a biocompatible hub for collecting the viscous liquid during heat sterilization. A distal end of the biocompatible hub, where the hub connects to the needle or other elongate tube, optionally has an internal funnel shaped surface which allows for simple flow of the viscous liquid back into the elongated tube after the heat sterilization is completed. During sterilization, the applicator is preferably held with the distal end of the elongate tube pointing downwards, to minimize an amount of the viscous liquid that leaves the elongate tube.

In other embodiments, the seeds are provided within a sealed capsule filled with glycerine in a predetermined location designed to allow easy loading of the seed into a needle. The capsule has a needle adaptor head defined to receive a needle into the capsule, in an orientation which loads the seed into the needle along with some of the glycerine. The brachytherapy seeds are thus protected by the viscous liquid throughout delivery and loading into a needle or other applicator.

An aspect of some embodiments of the invention relates to loading brachytherapy seeds into a needle applicator from a distal end of the needle (i.e., the end inserted into a patient), rather than from a proximal end. Loading the needle from the distal end reduces the distance that the seeds need to pass within an internal channel of the applicator and the possible damage from such passage.

An aspect of some embodiments of the invention relates to a capsule for loading brachytherapy seeds into an applicator. The capsule is configured to hold a brachytherapy seed within a closed chamber. Optionally, a first end of the chamber is adapted to receive a needle and the other end includes a piston configured to push the seed into a needle received through the first end.

An aspect of some embodiments relates to an applicator device having a non-metallic tube configured to carry one or more alpha-emitting brachytherapy seeds into human tissue. The non-metallic tube is configured to prevent emission of alpha radiation out of the tube, and thus prevents premature emission of radiation on healthy tissue. The use of a non-metallic tube allows use of imaging modalities, such as ultrasound, to accurately position the seeds, while they are inside the tube and prevented from emitting alpha radiation to healthy tissue. Optionally, the seeds are distanced from a distal tip of the tube by at least 3 millimeters, at least 5 millimeters or even at least 9 millimeters, to prevent radiation leakage through the tip of the tube.

Optionally, the applicator tube is removed from the patient tissue after the location of the seeds within the tumor is confirmed, for example, by ultrasound or computer tomography (CT). The removal of the tube activates the brachytherapy treatment, in that alpha and daughter nuclei from the seeds can now reach the patient tissue. The transparent elongate tube optionally comprises a polymer, such as Kapton. Alternatively, the tube is formed of any other suitable bio-compatible polymer which is durable in heat and/or radiation levels used for sterilization, such as biocompatible Polyether Ether Ketone (PEEK).

In some embodiments, the applicator device includes a mechanism for controlling the location of the seeds within the elongate tube relative to the distal end of the tube. Optionally, in an initial state, the seeds are held within the elongate tube at a distance from the distal end of the elongate tube. A sealing cap prevents Radon or other materials from exiting the distal end of the tube. After the location of the distal end of the tube relative to the tumor is verified, the applicator device is used to bring the seeds to the distal end of the elongate tube. Thereafter, the elongate tube is retracted proximally leaving the seeds in their location in the patient.

An aspect of some embodiments relates to a stopper for controlling the movement of a stylet relative to an elongate tube of an applicator, which has at least one state which limits or prevents both proximal and distal movement. Optionally, the stopper additionally has at least one state in which the stopper limits only distal movement and not proximal movement.

An aspect of some embodiments of the invention relates to a brachytherapy implant including one or more tubular-shaped seeds carrying particle emitters, mounted on a delivery wire. In some embodiments of the invention, the delivery wire comprises a hollow tube. The use of a hollow tube as a delivery wire allows simple anchoring of the wire by pressing on the wire in a manner which causes portions of the wire not pressed on to bulge outwards.

An aspect of some embodiments relates to a method of implanting brachytherapy seeds in a patient. The method involves inserting a delivery strand carrying the seeds into a body organ, in a needle which enters the organ from one side and exits from a different side. A physician grasps a distal end of the delivery strand and adjusts the location of the seeds by moving the distal end of the delivery strand.

In some embodiments, the needle is inserted into the organ with the delivery strand enclosed within the needle. Alternatively, the strand is inserted into the needle after the needle is inserted into the organ. For example, the delivery strand may be passed within a flexible tube into a separate needle previously inserted into the body organ.

Figure 1:
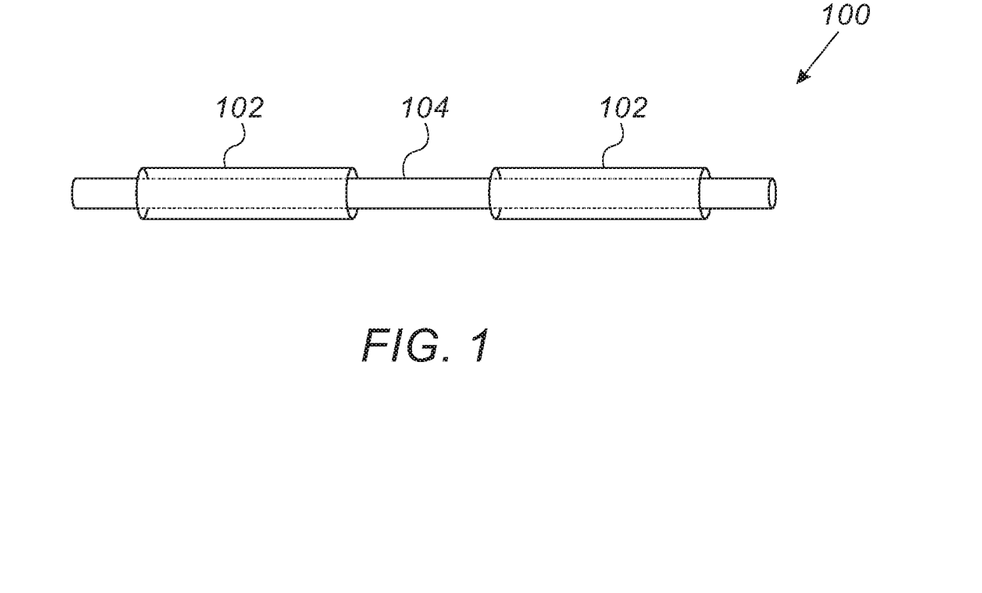
FIG. 1 is a schematic illustration of a diffusing alpha-emitter radiation therapy (DaRT) implant, in accordance with an embodiment of the invention.

FIG. 1 is a schematic illustration of a diffusing alpha-emitter radiation therapy (DaRT) implant 100, in accordance with an embodiment of the invention. Implant 100 comprises a delivery wire 104 with one or more brachytherapy seeds 102 mounted thereon. Each seed 102 comprises a cylindrical tube with an internal tunnel in which delivery wire 104 is passed. While in FIG. 1 delivery wire 104 is shown with two seeds 102, delivery wire 104 may be threaded with any suitable number of seeds, including through a single seed 102 or a plurality of seeds 102, possibly more than three or even more than five, depending on the needs of the specific patient. Delivery wire 104 is optionally flexible, such that in the areas along its length not covered by seeds 102 it can bend as needed to fit into a patient. The mounting of the seeds on wire 104 allows insertion of a plurality of seeds 102 into a patient together. Delivery wire 104 may be used to anchor seeds 102 in place within a patient and/or may be used to remove the seeds 102 from the patient, after a treatment session.

Each seed 102 optionally has a length of at least 0.2 centimeters, 0.5 centimeters or even at least 0.8 centimeters. Optionally, seed 102 is shorter than 2.1 centimeters, or even shorter than 1.5 or 1.2 centimeters. In some embodiments, seed 102 has a length of about 1 centimeter. The seed optionally has an outer diameter of at least 0.3 millimeters, at least 0.5 millimeters, or even at least 0.6 millimeters. In some embodiments, seed 102 has an outer diameter of about 0.7 millimeters, while in other embodiments seed 102 has an outer diameter of 0.35 millimeters. The inner diameter of seed 102 is optionally greater than 0.2 millimeters, greater than 0.4 millimeters or even greater than 0.5 millimeters. In some embodiments, the inner diameter of seed 102 is smaller than 2 millimeters, smaller than 1 millimeter or even smaller than 0.5 millimeters. In some embodiments, the internal diameter is about 0.25 millimeters or 0.4 millimeters. The Tubular seeds 102 optionally have a length of at least 2 times, at least 5 times or even at least ten times their outer diameter. Seed 102 optionally comprises stainless steel, for example 316LVM stainless steel, Titanium, Nitinol and/or any other suitable biocompatible conducting material.

Delivery wire 104 has an outer diameter of about the size of the inner diameter of seed 102. In some embodiments, the outer diameter of wire 104 is smaller than the inner diameter of seed 102, so that wire 104 moves freely within the seed. In other embodiments, the diameter of wire 104 is substantially equal to the inner diameter of seed 102, so that seed 102 does not move relative to wire 104 without applying at least a predetermined force. The difference between the inner diameter of seeds 102 and the outer diameter of wire 104 is optionally greater than 5 microns, greater than 15 microns or even greater than 25 microns. The difference between the inner diameter of seeds 102 and the outer diameter of delivery wire 104 is preferably smaller than 60 microns, smaller than 40 microns or even smaller than 30 microns.

Wire 104 optionally comprises a metal, such as nitinol or stainless-steel, for example 316LVM stainless steel. Alternatively, wire 104 comprises a bio-compatible string-suture. For example, delivery wire 104 may comprise a polymer thread, such as polypropylene, polyester, Polytetrafluoroethylene (PTFE) and/or PEEK. Delivery wire 104 is optionally formed of a biodegradable material. Alternatively, delivery wire 104 is not biodegradable, such that delivery wire 104 can be used to remove seeds 102 from the patient after a treatment interval. The treatment interval is optionally at least a week, at least a month or even at least three months.

Optionally, the seeds 102 are fixed to delivery wire 104 to prevent their sliding on delivery wire 104, using any suitable method known in the art. In some embodiments, delivery wire 104 comprises a biocompatible polymer thread which is inflated to prevent seed 102 from sliding along delivery wire 104. Alternatively or additionally, the seeds 102 are fixed on delivery wire 104, by distortion of delivery wire 104, e.g., forming a knot, at the ends of the seed 102.

In some embodiments, delivery wire 104 is formed of a material which expends when heated. After delivery wire 104 is inserted into one or more seeds 102 it is heated so that the wire is fixed to the seeds. In some embodiments, delivery wire 104 comprises a hollow tube, which can be easily deformed by a physician, in a manner which can be used for anchoring of the delivery wire 104, as discussed hereinbelow.

The seeds 102 on delivery wire 104 may be distanced from each other or may be adjacent each other, with a very small space between the ends of adjacent seeds 102 (e.g., less than 0.5 millimeters or even less than 0.05 millimeters).

In some embodiments, the one or more seeds 102 are mounted in the middle of delivery wire 104, in a manner leaving free ends of delivery wire 104 on both sides of the seed 102. Optionally, the ends of delivery wire 104 not covered by seed 102 have a length of at least 5 millimeters, at least 10 millimeters or even at least 20 millimeters. The physician can thus use both ends of delivery wire 104 to adjust the location of the seeds 102 within a tumor and/or to fixate the seeds 102 within the tumor. In addition, after a treatment duration, delivery wire 104 may be used to remove the seeds 102 from the patient.

In other embodiments, the one or more seeds 102 are mounted on an end of delivery wire 104 which serves as a tail for adjustment and/or fixation of the seed locations and/or removal of the seeds after treatment is completed.

Seed 102 is loaded with particles of a radioactive substance. Optionally, the radioactive substance comprises alpha emitting atoms on an outer surface of seed 102. The particles are mounted on the seed using any method known in the art, including any of the methods described in U.S. Pat. No. 8,834,837 to Kelson et al., titled: "Method and Device for Radiotherapy", and US patent publication 2009/0136422 to Kelson et al., titled: "Radioactive Surface Source and a Method for Producing the Same", which are incorporated herein by reference in their entirety. In some embodiments, the seeds carry Radium-223 or Radium-224 particles. Alternatively, the seeds carry other suitable particles, such as Radon-219, Radon-220 or Thorium-228. Optionally, seed 102 comprises up to 5 µCi and/or up to 185 kBq of Radium 224. It is noted, however, that in other embodiments, seed 102 is loaded with other amounts of radioactive substances or with other radioactive substances which emit other particles, such as beta and/or gamma particles.

Figure 2:
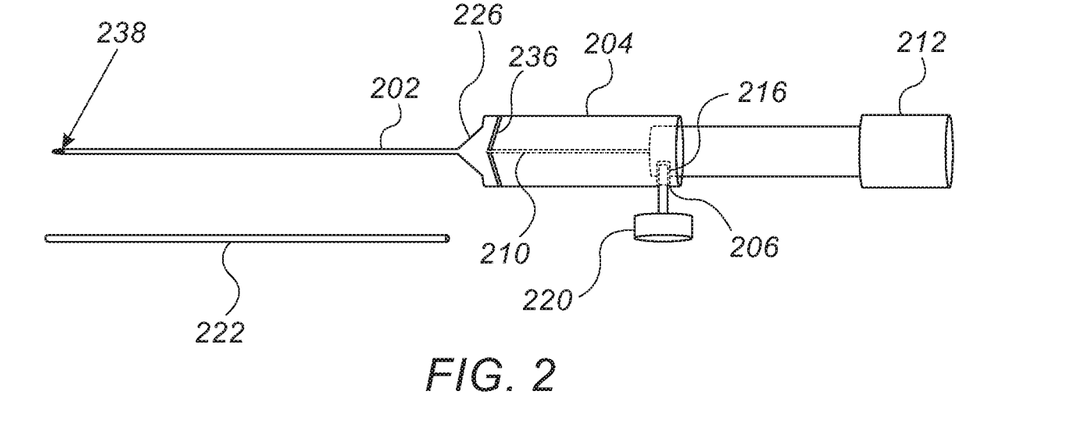
FIG. 2 is a schematic illustration of an applicator for delivering one or more seeds to a location in a patient, in accordance with an embodiment of the invention.

FIG. 2 is a schematic illustration of an applicator 200 for delivering one or more seeds 102 to a location in a patient, in accordance with an embodiment of the invention. Applicator 200 comprises an elongated hollow tube 202, configured to receive implant 100, and having a proximal tube hub 204 serving as a handle. Applicator 200 further comprises a stylet 210 configured to be inserted into elongated hollow tube 202. Stylet 210 has a proximal stylet hub 212, which at least partially fits into a hollow channel within tube hub 204. Optionally, a safety screw 220 is used to fixate an aperture 206 in tube hub 204 to a corresponding aperture 216 in stylet hub 212, and thus lock a distal end of stylet 210 at a predefined location within tube hub 204 or within a proximal portion of elongated hollow tube 202. A protective cap 222 optionally covers the elongated tube 202, during handling.

In some embodiments, elongated hollow tube 202 comprises a rigid needle, for example a stainless-steel needle. Alternatively, elongated hollow tube 202 comprises a flexible tube, such as a Kapton tube, for example a transparent Kapton tube allowing a physician to see the seeds 102 within elongated hollow tube 202. Optionally, in accordance with this alternative, in order to insert tube 202 into a patient, a separate hollow needle of any desired shape (e.g., straight, curved) is inserted into the patient, and tube 202 is inserted into the separate needle.

Delivery wire 104 is optionally held entirely within elongated tube 202. In order to insert the one or more seeds 102 on delivery wire 104 into a patient, elongated tube 202 is brought to the desired implant location. Then, safety screw 220 is removed and stylet 210 is pushed forward in a manner which pushes a distal portion of delivery wire 104 out of a distal end of elongated tube 202. The use of stylet 210 to push delivery wire 104 out of elongated hollow tube 202, allows seeds 102 to be distanced from the distal end of elongated tube 202 during shipment and before actual use, in a manner which prevents undesired radiation leakage. Optionally, during shipment, the distal end of the most distal seed 102 in elongated hollow tube 202 is distanced from the distal end of elongated hollow tube 202 by at least 1 centimeter or even 1.5 centimeters.

Stylet 210, in some embodiments, is shorter than needle 202, such that the distal tip of stylet 210 does not reach the distal end of needle 202. Optionally, stylet 210 has a length suitable to push delivery wire 104 distally up to a point in which a small distal portion of delivery wire 104 protrudes out of needle 202. Stylet 210 optionally has a sufficient length to push a proximal end of delivery wire 104 to a point at which a distal end of delivery wire 104 slightly protrudes from needle 202. The extent to which delivery wire 104 protrudes from needle 202 after being pushed by stylet 210 is optionally less than 20 millimeters, less than 10 millimeters or even less than 8 millimeters. The length of stylet 210 is optionally a little longer than the difference between the length of needle 202 and a shortest delivery wire 104 considered to be placed in needle 104. Alternatively, stylet 210 has a length suitable to push a seed 102 to a distal end of needle 102, for example, having a length equal to the difference between the length of needle 202 and seed 102. The use of a short stylet is particularly feasible in cases in which the needle is inserted into a body organ where it exits from an opposite side of the body organ. In such cases, a physician has simple access to the distal end of the delivery wire 104 that protrudes from the needle 202, and can thus adjust the location of the seed 102, without using stylet 210.

In some embodiments, applicator 200 is provided with an entrance seal 236 at a proximal end of elongated tube 202 or in a distal portion of tube hub 204, near the proximal end of elongate tube 202. Entrance seal 236 prevents Radon gas, developing in elongate tube 202, from exiting elongated tube 202 proximally. Optionally, entrance seal 236 comprises a Wilson seal, which preserves its sealing attributes even when stylet 210 is passed through entrance seal 236 into elongate tube 202. Alternatively, entrance seal 236 comprises a stretched foil. Further alternatively, entrance seal 236 comprises any other suitable seal, such as any suitable seal described in G. M Hofz. "A survey of Actuator Shaft Sealing Techniques for Extended Space Missions", National Aeronautics and Space Administration, Dec. 15, 1972, the disclosure of which is incorporated herein by reference. Applicator 200 optionally also includes a distal seal 238, at a distal end of elongate tube 202. Distal seal 238 includes, for example, a bee-wax plug or a bio-compatible foil, which prevents exit of Radon gas from the distal end of elongate tube 202. Alternatively, any other suitable sealing material, which can easily be removed when implant 100 is to exit elongate tube 202, may be used.

Figure 3:
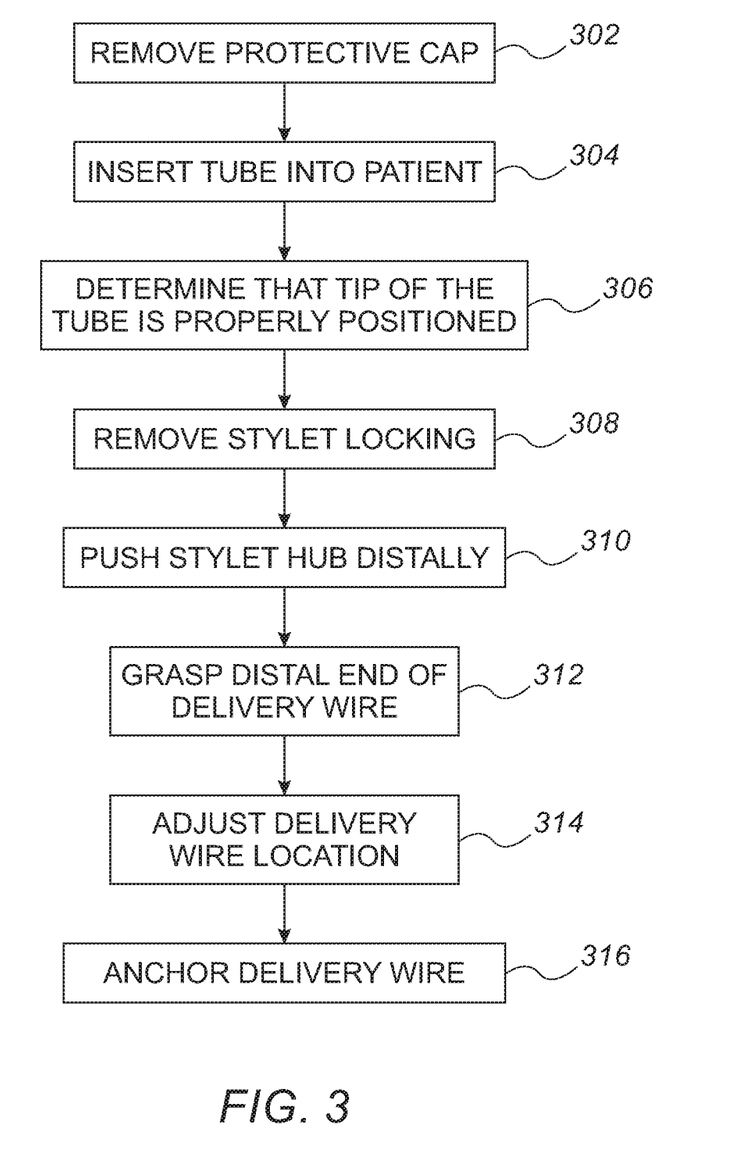
FIG. 3 is a flowchart of acts performed in delivering a DaRT implant to a tumor in a patient's arm, in accordance with an embodiment of the invention.
Figure 4A:
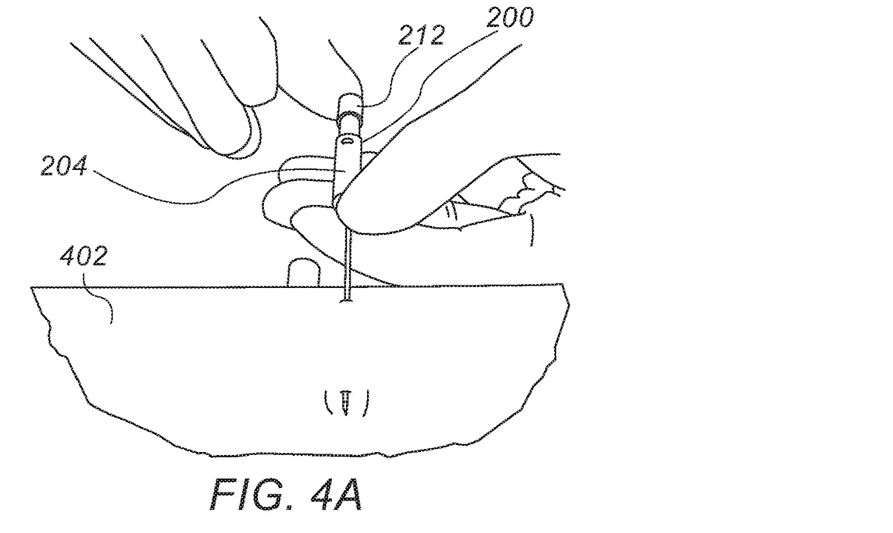
FIG. 4A is a schematic illustration of an applicator during delivery of a DaRT implant to a tumor in a patient's arm, in accordance with an embodiment of the invention.

FIG. 3 is a flowchart of acts performed in delivering a DaRT implant to a tumor in a patient's arm 402 (FIG. 4), in accordance with an embodiment of the invention. The implant process begins with removing (302) protective cap 222 from the applicator elongated hollow tube 202 (FIG. 2). The elongated hollow tube 202 is inserted (304) into the patient's arm where the tumor is located. In embodiments in which elongated hollow tube 202 is a needle, the needle is directly inserted into the arm. In other embodiments, a separate needle is inserted into the patient's arm, and elongated hollow tube 202 is inserted into the separate needle.

When it is determined (306) that the distal end of elongated hollow tube 202 is properly positioned, the locking of stylet 210 relative to elongated hollow tube 202 is removed (308), for example, by removal of safety screw 220. Then, while holding tube hub 204, stylet hub 212 is pushed (310) distally, in a manner which causes a distal end of stylet 210 to push implant 100 distally and thus cause a distal end of delivery wire 104 to exit elongated tube 202.

FIG. 4A is a schematic illustration of applicator 200 during delivery of a DaRT implant to a tumor in a patient's arm 402, in accordance with an embodiment of the invention. FIG. 4A shows applicator 200 after stylet hub 212 is pushed (310) distally.

A physician grasps (312) the distal portion of delivery wire 104, for example using forceps, and applicator 200 is removed proximally from the patient, while leaving delivery wire 104 and the one or more seeds 102 thereon within the patient's arm 402. Delivery wire 104 is moved, if necessary, to adjust (314) its location, and when properly positioned delivery wire 104 is anchored (316) in place.

In some embodiments, the anchoring (316) is achieved using fixation buttons on both sides. Any suitable fixation buttons may be used, such as the buttons described in U.S. Pat. No. 2,075,508 to Davidson, titled: "Suture Retainer", the disclosure of which is incorporated herein by reference in its entirety. Optionally, after placing a fixation button on an end of wire 104, the wire is deformed adjacent the button to keep the button urged against the patient. As mentioned above, in some embodiments, wire 104 comprises a hollow tube. In these embodiments, wire 104 is optionally deformed by pressing against the wire using forceps or any other suitable tool, which causes the sides of the wire to which pressure was not applied to bulge outwards.

Figure 4B:
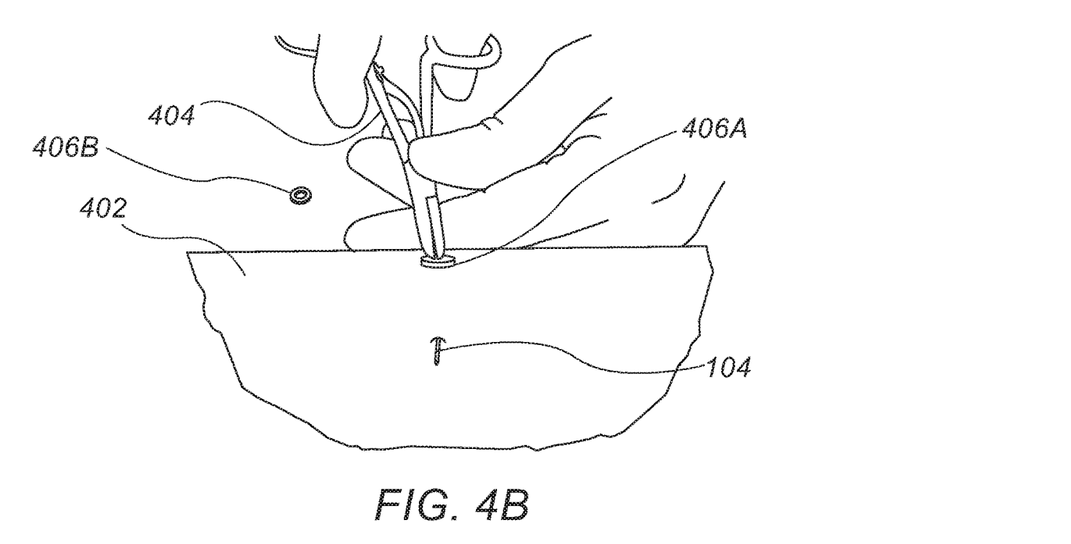
FIG. 4B is a schematic illustration of anchoring an implant in a patient's arm, in accordance with an embodiment of the invention.

FIG. 4B is a schematic illustration of anchoring an implant 100 (FIG. 1) in a patient's arm 402, in accordance with an embodiment of the invention. FIG. 4B shows a first button 406A already placed on a proximal end of delivery wire 104 and a second button 406B ready for installation. In order to anchor the button, forceps 404 are used to press on a clip which locks the button in place. Alternatively, a button which serves as a clip is used, as described below with reference to FIG. 10, and forceps 404 are used to press on the button. Further alternatively, delivery wire 104 itself is deformed to fixate the button in place. In embodiments in which delivery wire 104 is hollow, the pressure on the delivery wire deforms the wire in a manner which causes the wire to cave in at the points at which the pressure is applied and to bulge out where pressure is not applied. This prevents the button 406A from falling off the delivery wire 104. In other embodiments, the anchoring is achieved by bending delivery wire 104 sideways. In embodiments in which delivery wire 104 comprises a flexible suture, the anchoring is optionally achieved by tying the suture.

Alternatively or additionally to use of entrance seal 236 and/or distal seal 238 in order to prevent radiation from seeds 102 from being released during handling, hollow tube 202 is filled with a viscous liquid that prevents release of Radon particles. In addition, the viscous liquid generates a vacuum effect which allows suction of a seed 102 which partially exited hollow tube 202 back into hollow tube 202, when determined that the seed is not properly located. This vacuum effect is especially usefully with embodiments in which hollow tube 202 is metallic and other means described herein for accurate positioning of the seeds 102 are not used. Optionally, after determining that the tip of the needle and seed 102 are properly located (306) using the available means, the physician pushes stylet 210 an amount required to have the seed partially exit the distal tip of tube 202. The location of the seed 102 is then verified and a decision is made as to whether to proceed with pushing the seed out of elongate tube 202 or to suck the seed 102 back into elongate tube 202 and adjust the location of the tip of tube 202 for a more accurate release of seed 102.

The viscous liquid optionally comprises a biocompatible material which can withstand sterilization at about 160 degrees Celsius. In some embodiments, the viscous liquid has a viscosity of at least 10, 20 or even 50 centipose (cP) at 20 degrees Celsius. Optionally, the viscous liquid comprises glycerin, for example USP class VI glycerin. The glycerin optionally has a water content of less than 5%, less than 2% or even less than 1%. In some embodiments, proximal tube hub 204 defines an internal empty chamber designed to collect excess viscous liquid from elongated hollow tube 202 when the viscous liquid expands due to heat sterilization. Optionally, a distal end of proximal tube hub 204, connecting to the elongated tube 202, has a funnel shape 226 configured to allow viscous liquid from the elongated tube entering hub 204 to return to the elongated tube 202.

The glycerine is optionally loaded into elongated hollow tube 202 from the distal end of elongated hollow tube 202. A syringe holding glycerine is optionally connected to the distal end of elongated hollow tube 202 and glycerine from the syringe is pushed into tube 202.

The viscous liquid may fill elongated hollow tube 202 entirely, or only a portion of tube 202 surrounding seeds 102. Optionally, the viscous liquid covers at least 10 millimeters from each side of seeds 102.

Figure 5:
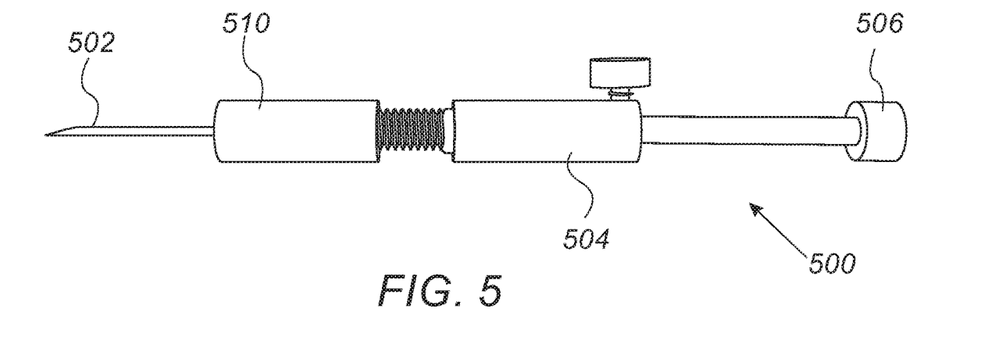
FIG. 5 is a schematic illustration of an applicator, in accordance with another embodiment of the invention.

FIG. 5 is a schematic illustration of an applicator 500, in accordance with another embodiment of the invention. Similarly to applicator 200, applicator 500 comprises a needle 502, a needle hub 504, a stylet hub 506 and a stylet (not shown) at a distal end of the stylet hub 506, within needle hub 504. Applicator 500 differs from applicator 200 in that its stylet is longer and is intended to have a length of about the length of needle 502, allowing a physician to push the entire content of needle 502 out of the needle. Thus, applicator 500 can be used to insert one or more seeds to a patient, in locations in which needle 502 does not exit the patient from an opposite side and does not allow pulling of the seed 102 and/or delivery wire 104 from the opposite side. In some embodiments, applicator 500 includes a depth adaptor 510 which is used to adjust the length of needle 502 that is inserted into the patient. Optionally, the depth is adjusted by rotating depth adaptor 510 around a threading on an external surface of needle hub 504.

Applicator 500 is used, in some embodiments, together with a template which defines the locations in which the seeds are to be inserted, as described for example in US patent publication 2017/0319871 to Pitman, titled: "Brachytherapy Fiducial Needle Fixation System" and/or in US patent publication 2014/0296612 to Schwartz, titled: "Brachytherapy Assist Device", the disclosures of which are incorporated herein by reference in their entirety.

In some embodiments, applicators 200 and/or 500 are supplied to physicians preloaded with one or more seeds 102. In these embodiments, the physician only needs to insert the needle of the applicator into the patient. In other embodiments, the physician loads one or more seeds 102 into the needle. The needle of applicator 200 and/or 500 is optionally supplied without any preloaded seeds 102 and the physician loads a desired number of seeds 102 into the needle. Alternatively, the needle is supplied preloaded with a minimal number of seeds, e.g., one seed, and the physician loads one or more additional seeds, when required.

Figure 6:
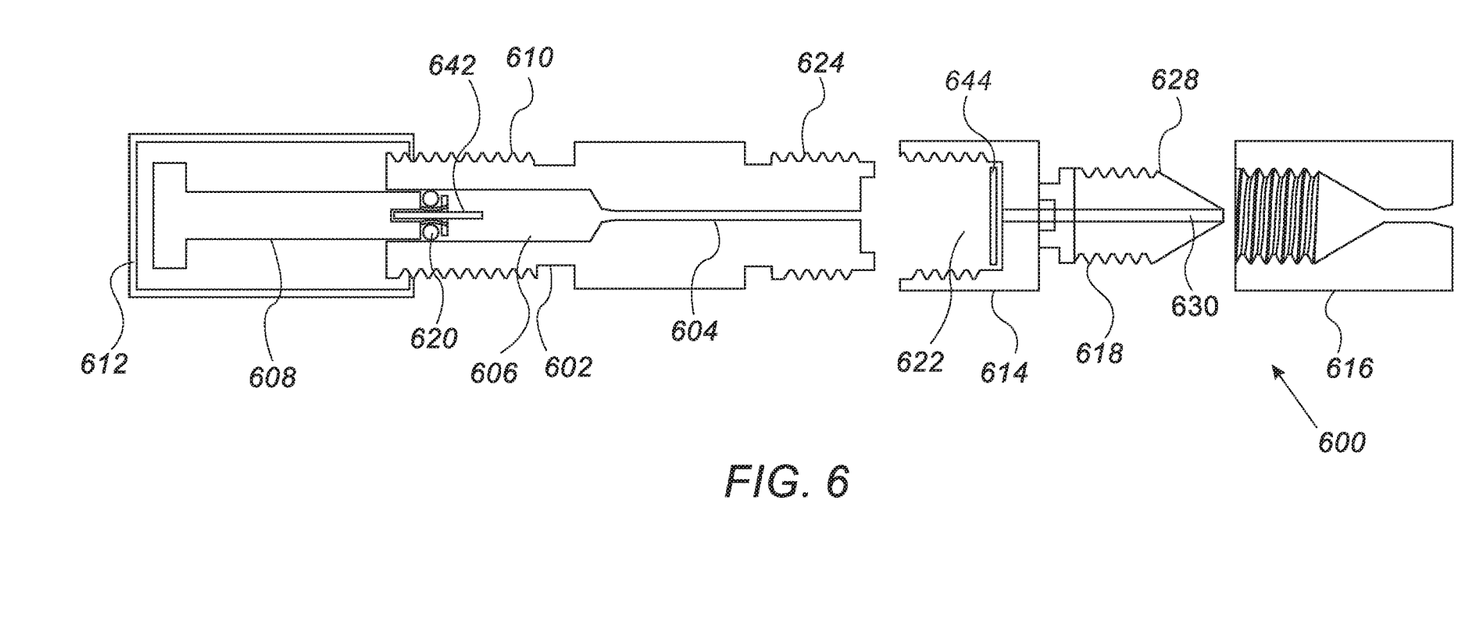
FIG. 6 is a schematic illustration of a seed vial, in accordance with an embodiment of the invention.

FIG. 6 is a schematic illustration of a seed vial 600, in accordance with an embodiment of the invention. Seed vial 600 comprises a tube 602, which defines on one side a narrow central chamber 604, designed to store a brachytherapy seed 102, and on an opposite side a wide chamber 606 configured to receive a piston 608, which carries a stylet 642 designed to push the seed 102 held within narrow chamber 604 into a needle. An O-ring 620 is optionally positioned toward the end of piston 608 so that when piston 608 is pushed into chamber 606, liquid in the wide chamber 606 is pushed into narrow chamber 604. The outer side of tube 602, on the side of wide chamber 606, optionally defines a threading 610, which is matched by a piston screw 612, which can be screwed onto the threading 610 in a manner which pushes piston 608 into chamber 606. Seed vial 600 further includes a needle adapter 614 and a needle screw 616, which serve as a port for receiving a needle into seed loading device 600. Needle adapter 614 includes, on one side, a receptacle 622 with an internal threading which screws onto a corresponding threading 624 on tube 602. On an opposite end, needle adapter 614 comprises an elastic member 628, having an external threading 618. When an internal screw of needle screw 616 is screwed onto external threading 618 of needle adapter 614, elastic member 628 is pressed inwards and narrows an internal needle channel 630 of needle adapter 614. When a needle is in needle channel 630, the pressure on elastic member 628 prevents the needle from moving.

Tube 602 is optionally filled with glycerine, which prevents radiation from seed 102 from escaping out of seed vial 600. Seed vial 600 is provided with piston screw 612 screwed over only a limited end portion of threading 610 and needle screw 616 screwed only over a limited end portion of threading 618. In order to load the seed 102 within seed vial 600 into a needle, the needle is inserted through needle screw 616 and needle adapter 614 into narrow chamber 604 of tube 602. The needle is then locked in place by tightening needle screw 616 over needle adapter 614. Then, piston screw 612 is screwed onto threading 610 in order to push piston 608 towards the needle and thus push seed 102 along with some of the glycerine in tube 602, into the needle. Needle screw 616 is then released and the needle is taken out of seed vial 600. In some embodiments, a silicone seal 644 is placed in receptacle 622, to prevent leakage from tube 602. In some embodiments, seed vial 600 contains about 10 milliliters of glycerine.

It is noted that instead of threading 610 and piston screw 612, any other suitable means may be used to push piston 608 into wide chamber 606.

The loading of seeds 102 into applicator 200 and/or 500 using seed vial 600 is through the distal end of elongate hollow tube 202. Loading from the distal end may also be performed when the loading is performed by the manufacturer of applicator 200 and the applicator is provided to the physician preloaded. Loading seeds 102 into applicator 200 from the distal end reduces the distance that the seeds 102 need to pass within an internal channel of the applicator and the possible damage from such passage. It is noted that in some cases the applicator has an internal channel longer than a meter or even longer than 1.5 meters and the passage of the seeds through a narrow channel of such a length may rub off a substantial percentage of the radioactive nuclides on the seeds. The loading from the distal end is particularly important when the seeds 102 provide alpha radiation, which are usually not covered by a substantial protective cover.

In the above description, the stylet of applicators 200 and 500 has two states. In a first state, safety screw 220 holds the stylet retracted, and implant 100 is entirely in elongated tube 202, while in a second state, after safety screw 220 is removed, the stylet is pushed forward to push a portion or the entirety of implant 101 out of elongated tube 202. In some embodiments, it is desired to define three or more states for stylet 210. In a first state, the stylet is retracted and the distal seed 102 in elongated tube 202 is distanced from the end of elongated tube 202 to prevent radiation from exiting elongated tube 202. In a second state, the distal seed 102 within elongated tube 202 is brought to the distal end of elongated tube 202, allowing a physician to easily know the location of the distal seed. In a third state, the elongated tube 202 is retracted such that the stylet 210 is located in a most distal location relative to elongated tube 202. While these states could be achieved by careful manual control by a physician, in some embodiments, an applicator is provided with a mechanism for maintaining the applicator in the three different states. It is noted that although the present description relates to three states, in some embodiments the mechanisms used for maintaining the applicator in a plurality of states allow for more than three states.

Figure 7A:
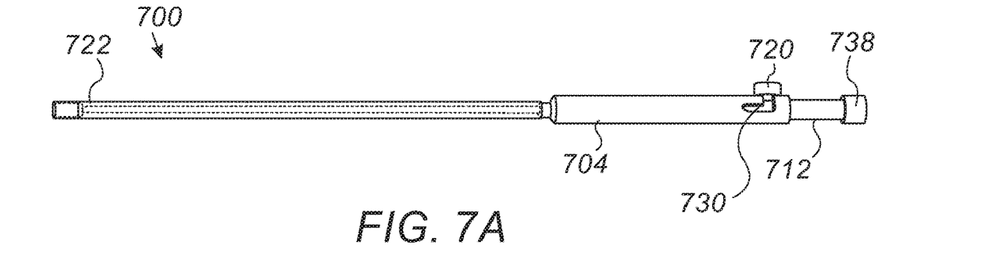
FIG. 7A is a schematic illustration of an applicator, in accordance with an embodiment of the invention.
Figure 7B:
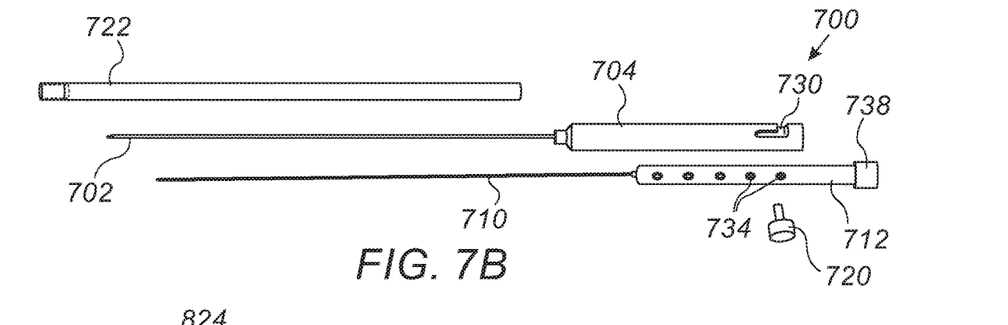
FIG. 7B is a schematic illustration of the components of the applicator of FIG. 7A, in accordance with an embodiment of the invention.

FIG. 7A is a schematic illustration of an applicator 700, in accordance with an embodiment of the invention. FIG. 7B is a schematic illustration of the components of applicator 700, in accordance with an embodiment of the invention. Applicator 700 comprises a needle 702 which carries one or more seeds 102 (FIG. 1) and has a proximal needle hub 704. Applicator 700 further comprises a stylet 710, having a stylet hub 712. Needle hub 704 defines a slot 730 configured to receive a safety screw 720, used to lock a relative orientation of stylet 710 within needle 702, in a plurality of different states. Slot 730 optionally has an upside-down L shape. Stylet hub 712 defines one or more apertures 734 adapted to receive safety screw 720. Optionally, apertures 734 have internal threading configured to receive screw 720. Alternatively, apertures 734 have any other structure suitable for locking screw 720. As shown, stylet hub 712 defines a plurality of apertures 734, at different positions along the length of the stylet hub. A physician may select use of one of the apertures 734 in which to pass screw 720, according to the number and/or length of seeds 102 to be placed in needle 702.

In a first state, screw 720 is placed in the leg of L-shaped slot 730 at a most proximal position on needle hub 704. In this state, seeds 102 are located within needle 702, distanced from a tip of needle 702. In a second state, screw 720 is located in the head of L-shaped slot 730 at the most distal point of the slot. In the second state, the distal end of stylet 710 is in a position which pushes seeds 102 to the tip of needle 702. In a third state, screw 720 is removed and needle 702 is retracted toward a proximal end 738 of stylet hub 712, leaving seeds 102 in the patient.

Figure 8A:
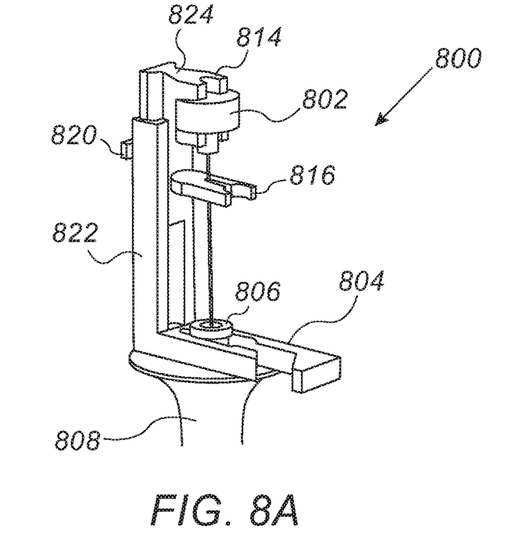
FIGS. 8A and 8B are schematic illustrations of an external stopper used to hold a stylet and a needle in a plurality of different relative states, in accordance with an embodiment of the invention.
Figure 8B:
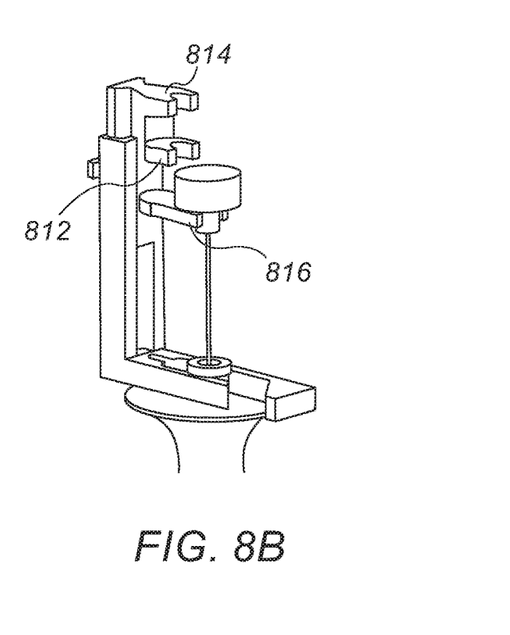

FIGS. 8A and 8B are schematic illustrations of an external stopper 800 used to hold a stylet and a needle in a plurality of different relative states, in accordance with an embodiment of the invention. Stopper 800 comprises a plurality of arm pairs designed to grasp a stylet hub 802. Stopper 800 further comprises a lower slot 804 designed to accept a proximal notch 806 of a needle hub 808. In a first state, stylet hub 802 is held between a top pair of arms 814 and an upper pair of arms 812, as shown in FIG. 8A. In the first state, the stylet is prevented from moving distally and prematurely pushing one or more seeds 102 out of the needle. In addition, the stylet is prevented from moving proximally, i.e., backwards, when the needle is inserted to patient tissue.

When desired to push a seed 102 to a distal tip of the needle, stylet hub 802 is pushed out of the recess defined by arm pairs 812 and 814 onto a lower pair of arms 816. Optionally, the lower pair of arms 816 is longer than the upper pair of arms 812, such that stylet hub 802 is easily moved from the first state to the second state. To move to a third state, external stopper 800 is removed from needle hub 808, allowing retraction of the needle onto the stylet.

Optionally, the length of stopper 800 from lower slot 804 to top pair of arms 814 is adjustable, using knob 820. In some embodiments, stopper 800 comprises two separate parts which are slideable relative to each other. A first part 822 includes an outer frame which defines lower slot 804 and a second part 824 includes arm pairs 812, 814 and 816. In some embodiments, notches are defined for predetermined adjustable sizes of stopper 800 corresponding to different numbers of seeds 102 in the needle.

Figure 9:
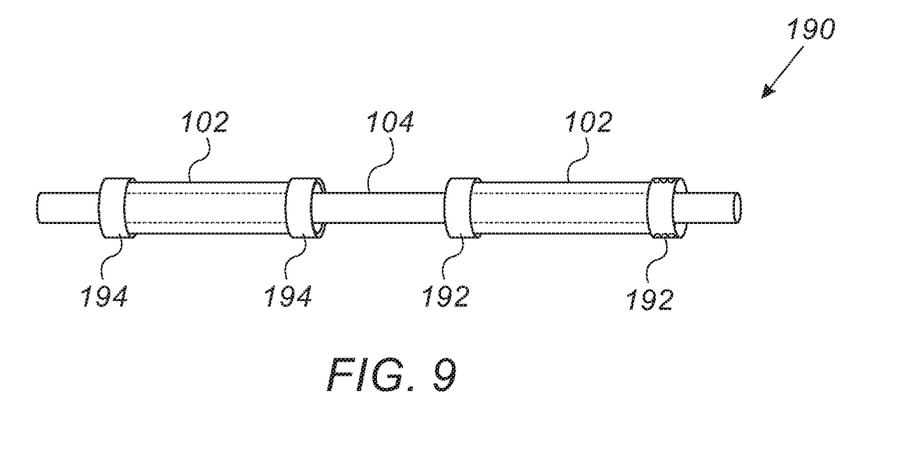
FIG. 9 is a schematic illustration of a diffusing alpha-emitter radiation therapy (DaRT) implant, in accordance with another embodiment of the invention.

FIG. 9 is a schematic illustration of a DaRT implant 190, in accordance with another embodiment of the invention. DaRT implant 190 is similar to implant 100 of FIG. 1 but includes on the edges of some or all of seeds 102 sealing rings, which prevent Radon from escaping out of the vicinity of the seeds. As shown, seed 102 on the left includes sealing rings 194 which are mounted entirely on the seed itself. Rings 194 have an external diameter configured to match the inner diameter of elongated tube 202 in a manner which seals the space between the seed 102 and the tube 202. The seal prevents radon gas leaving the radioactive nuclides on seed 102 from escaping elongated tube 202. The seed 102 on the right includes sealing rings 192 which are mounted partially on the seed 102 and partially on delivery wire 104. Accordingly, sealing rings 192 have two different internal radiuses, one to match delivery wire 104 and the other to match seed 102.

Sealing rings 192 and 194 optionally comprise silicone, for example USP class VI silicone. Alternatively, rings 192 and/or 194 comprise any other material suitable for sealing and preventing gas leakage. Sealing rings 192 and/or 194 are used instead of, or in addition to, entrance seal 236, distal seal 238 and/or the viscous liquid filling of elongate tube 202.

Figure 10:
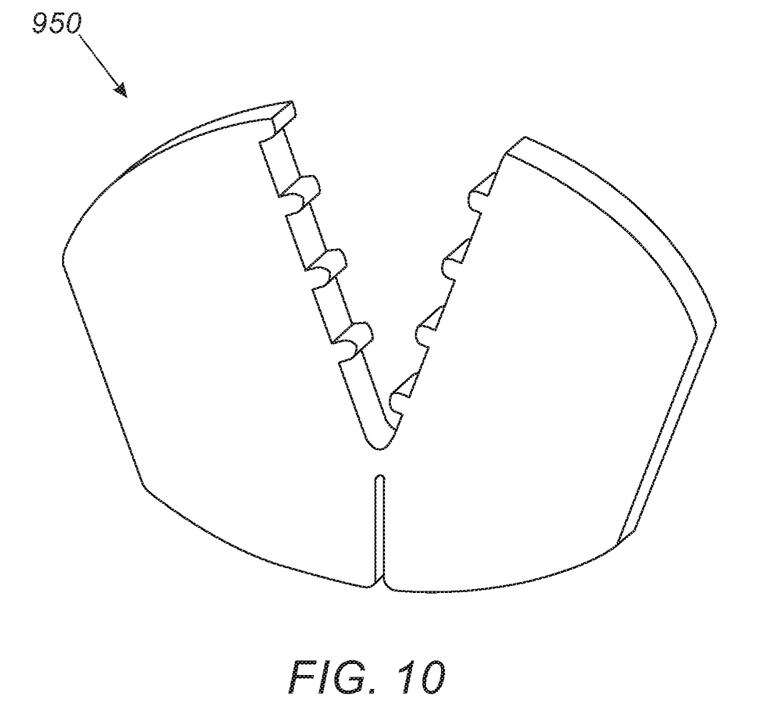
FIG. 10 is a schematic illustration of a button clip, in accordance with an embodiment of the invention.

FIG. 10 is a schematic illustration of a button clip 950, in accordance with an embodiment of the invention. Button clip 950 is optionally used to fixate delivery wire instead of buttons 406A and/or 406B. Button clip 950 comprises two half circles which are connected by a pivot and include notches which lock into each other. In order to lock button clip 950 onto delivery wire 104, the button clip is placed around the delivery wire 104 and the two halves are pushed toward each other to lock with delivery wire 104 between the halves.

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include." "have" and their conjugates, shall mean, when used in the claims, "including but not necessarily limited to."

The invention claimed is:

1. Apparatus for brachytherapy, comprising:
a casing;
one or more brachytherapy seeds for implanting in a patient, wherein the seeds are carrying atoms of an alpha-emitting radioactive element for radiotherapy treatment, within the casing; and
a viscous liquid within the casing, surrounding the one or more brachytherapy seeds in a manner preventing daughter nuclei of the atoms from exiting the casing.

2. The apparatus of claim 1, wherein the casing comprises a needle.

3. The apparatus of claim 1, wherein the viscous liquid comprises glycerine.

4. The apparatus of claim 1, wherein the casing comprises a seed applicator including a tube adapted for insertion into a patient and a stylet within the tube.

5. The apparatus of claim 4, wherein each of the one or more brachytherapy seeds has a length of at least 0.5 centimeters.

6. The apparatus of claim 1, wherein the casing comprises a seed capsule including a needle port on a first end and a piston carrying the one or more brachytherapy seeds on a second end, and wherein movement of the piston urges the one or more brachytherapy seeds into a needle in the needle port.

7. The apparatus of claim 6, wherein the needle port is configured to receive the needle in an orientation such that the one or more brachytherapy seeds enter the needle along with a portion of the viscous liquid.

8. The apparatus of claim 1, wherein each of the one or more brachytherapy seeds has a length of at least 0.2 centimeters.

9. The apparatus of claim 1, wherein each of the one or more brachytherapy seeds comprises a cylindrical tube having an outer diameter of at least 0.3 millimeters.

10. The apparatus of claim 1, wherein the one or more brachytherapy seeds comprise seeds formed of a conducting material.

11. The apparatus of claim 1, wherein when the viscous liquid enters a tumor, radioactive daughter nuclei of the alpha emitting atoms in the viscous liquid participate in the radiotherapy treatment of the tumor.

12. The apparatus of claim 1, wherein the viscous liquid can withstand sterilization at about 160 degrees Celsius.

13. The apparatus of claim 1, wherein the casing includes an opening through which the one or more brachytherapy seeds are pushed out of the casing.

14. Apparatus for brachytherapy, comprising:
a casing;
one or more brachytherapy seeds for implanting in a patient, carrying atoms of a radioactive element for radiotherapy treatment, within the casing; and
a viscous liquid within the casing, in a manner preventing radiation from-the one or more brachytherapy seeds from exiting the casing,
wherein the casing comprises a seed applicator including an elongated tube adapted for insertion into a patient and a stylet within the tube,
wherein the casing comprises a hub at a proximal end of the elongate tube, wherein the hub has an empty chamber configured to collect excess viscous liquid from the elongate tube when the viscous liquid expands due to heat sterilization.

15. The apparatus of claim 14, wherein a distal end of the hub connecting to the elongate tube has a funnel shape configured to allow viscous liquid from the elongate tube entering the hub to return back to the elongate tube.

16. A method of loading a needle with brachytherapy seeds, comprising:
grasping a needle, having a sharp tip for entering tissue, in a manner preventing movement of the needle;
bringing a brachytherapy seed to a point adjacent the tip of the needle;
pushing the brachytherapy seed forward into the needle, through the sharp tip; and
loading a viscous liquid into the needle, through the sharp tip.

17. The method of claim 16, wherein pushing the brachytherapy seed forward comprises pushing a stylet, which pushes the seed forward into the needle.

18. The method of claim 16, wherein the brachytherapy seed has a length of at least 0.2 centimeters.

19. A brachytherapy seed loading device, comprising:
a central chamber storing a brachytherapy seed carrying Radium;
a needle port, configured to lock a needle in an orientation such that a sharp tip of the needle is aligned with the brachytherapy seed in the central chamber; and
a piston configured to push the brachytherapy seed into the needle locked in the needle port,
wherein the central chamber additionally stores a viscous liquid, which prevents Radon released by the brachytherapy seed from leaving the loading device.

20. The device of claim 19, wherein the needle port includes a screw which when fastened locks the needle in the needle port.

21. The device of claim 19, further comprising a piston screw which when rotated pushes the piston toward the central chamber.

22. The device of claim 19, wherein the brachytherapy seed has a length of at least 0.2 centimeters.

23. A brachytherapy seed applicator, comprising:
a hollow needle;
a non-metallic elongated tube configured for insertion into tissue, within the hollow needle;
a hub at a proximal end of the tube;
one or more brachytherapy seeds carrying radioactive particles, within the tube; and
a stylet configured to be inserted into the tube and to push the one or more brachytherapy seeds to a distal end of the elongated tube.

24. The brachytherapy seed applicator of claim 23, wherein the one or more brachytherapy seeds carry alpha-emitting particles.

25. The brachytherapy seed applicator of claim 23, wherein one or more brachytherapy seeds carry Radium.

26. The brachytherapy seed applicator of claim 23, wherein the non-metallic elongated tube allows viewing of the one or more brachytherapy seeds in an ultrasound image of the applicator.

27. The brachytherapy seed applicator of claim 23, wherein the non-metallic elongated tube prevents daughter nuclei of the radioactive particles from exiting the non-metallic elongated tube.

28. The brachytherapy seed applicator of claim 23, wherein the one or more brachytherapy seeds are distanced from a distal tip of the non-metallic elongated tube by at least one centimeter.

29. The brachytherapy seed applicator of claim 23, wherein the non-metallic elongated tube comprises Kapton.

30. A method of inserting a brachytherapy seed into body tissue, comprising:
   inserting a needle into body tissue through a first point until a tip of the needle exits the tissue at a second point;
   pushing a distal end of a strand carrying one or more brachytherapy seeds out of the distal tip of the needle;
   grasping the distal end of the strand; and
   retrieving the needle proximally from the tissue while grasping the distal end of the strand, so that the one or more brachytherapy seeds remain in the tissue.

31. The method of claim 30, further comprising pulling the distal end of the strand to adjust a location of the one or more brachytherapy seeds in the tissue.

32. The method of claim 30, wherein grasping the distal end of the strand comprises grasping with forceps.

33. The method of claim 30, wherein inserting the needle into body tissue comprises inserting the needle with the strand therein.

* * * * *